United States Patent
Shirai et al.

(10) Patent No.: US 10,180,474 B2
(45) Date of Patent: Jan. 15, 2019

(54) MAGNETIC RESONANCE IMAGING APPARATUS AND QUANTITATIVE MAGNETIC SUSCEPTIBILITY MAPPING METHOD

(71) Applicant: Hitachi, Ltd., Tokyo (JP)

(72) Inventors: Toru Shirai, Tokyo (JP); Ryota Satoh, Tokyo (JP); Yo Taniguchi, Tokyo (JP); Hisaaki Ochi, Tokyo (JP); Takenori Murase, Tokyo (JP); Yoshitaka Bito, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/525,099

(22) PCT Filed: Oct. 19, 2015

(86) PCT No.: PCT/JP2015/079477
§ 371 (c)(1),
(2) Date: May 8, 2017

(87) PCT Pub. No.: WO2016/076076
PCT Pub. Date: May 19, 2016

(65) Prior Publication Data
US 2018/0059198 A1    Mar. 1, 2018

(30) Foreign Application Priority Data

Nov. 11, 2014   (JP) ................. 2014-228843

(51) Int. Cl.
*A61B 5/055*  (2006.01)
*G01R 33/24*  (2006.01)
(Continued)

(52) U.S. Cl.
CPC ............ *G01R 33/443* (2013.01); *A61B 5/055* (2013.01); *G01R 33/56* (2013.01);
(Continued)

(58) Field of Classification Search
CPC ............. G01R 33/443; G01R 33/5608; G01R 33/5602; G06T 11/003; A61B 5/055
See application file for complete search history.

(56) References Cited

U.S. PATENT DOCUMENTS 7,782,051 B2 *  8/2010  Haacke ............ G01R 33/56536
                                                    324/307
8,422,756 B2 *  4/2013  Haacke ................ G01R 33/443
                                                    250/339.07
(Continued)

FOREIGN PATENT DOCUMENTS

JP    2011-153976 A    8/2011
JP    2011153976 A  *  8/2011  ............... A61B 6/03
(Continued)

OTHER PUBLICATIONS

International Preliminary Report on Patentability received in corresponding International Application No. PCT/JP2015/079477 dated May 26, 2017.
(Continued)

*Primary Examiner* — Brenda C Bernardi
(74) *Attorney, Agent, or Firm* — Mattingly & Malur, PC

(57) ABSTRACT

Provided is a technique in calculating a magnetic susceptibility distribution by using an MRI, for reducing artifacts and noise and improving precision in the magnetic susceptibility distribution being calculated. According to this technique, a magnetic field distribution is obtained via a phase image from a complex image acquired through MRI. Under the constraint based on a relational expression between the magnetic field and the magnetic susceptibility, smoothing process is performed iteratively on the magnetic susceptibility distribution calculated from the magnetic field distribution. Specifically, a minimization process for minimizing through the iterative operation, an error function defined by a predetermined initial magnetic susceptibility distribution (Continued)

and the magnetic field distribution is performed, thereby calculating the magnetic susceptibility distribution. At this time, an updated magnetic susceptibility distribution calculated based on the error function during the minimization process is smoothed, every time the updated magnetic susceptibility distribution is calculated.

20 Claims, 9 Drawing Sheets

(51) Int. Cl.
G01R 33/44 (2006.01)
G01R 33/56 (2006.01)
G06T 11/00 (2006.01)

(52) U.S. Cl.
CPC ..... *G01R 33/5602* (2013.01); *G01R 33/5608* (2013.01); *G06T 11/003* (2013.01); *G01R 33/243* (2013.01)

(56) References Cited

U.S. PATENT DOCUMENTS

| | | | |
|---|---|---|---|
| 8,781,197 B2* | 7/2014 | Wang | G01R 33/54 382/131 |
| 9,165,386 B2 | 10/2015 | Sato et al. | |
| 2011/0044524 A1 | 2/2011 | Wang et al. | |
| 2011/0262017 A1 | 10/2011 | Haacke et al. | |
| 2014/0219533 A1 | 8/2014 | Sato et al. | |
| 2015/0168525 A1 | 6/2015 | Sato et al. | |
| 2015/0338492 A1 | 11/2015 | Sato et al. | |
| 2017/0035364 A1* | 2/2017 | Noguchi | A61B 5/055 |

FOREIGN PATENT DOCUMENTS

| | | | |
|---|---|---|---|
| WO | 2013/054718 A1 | 4/2013 | |
| WO | 2014/057716 A1 | 4/2014 | |
| WO | 2014/076808 A1 | 5/2014 | |
| WO | WO-2014076808 A1 * | 5/2014 | ......... G01R 33/5608 |

OTHER PUBLICATIONS

Shmueli et al. "Magnetic Susceptibility Mapping of Brain Tissue In Vivo Using MRI Phase Data", Magnetic Resonance in Medicine, 2009, vol. 62, pp. 1510-1522.
Tang et al., "Improving Susceptibility Mapping Using a Threshold-Based K-Space/Image Domain Iterative Reconstruction Approach", Magnetic Resonance in Medicine, 2013, vol. 69, pp. 1396-1407.
Liu et al., "Morphology enabled dipole inversion (MEDI) from a single-angle acquisition: comparison with COSMOS in human brain imaging", Magnetic Resonance in Medicine, 2011, vol. 66, pp. 777-783.
Yoneda, Innervision, 2013, vol. 28, No. 9, pp. 13-16.
International Search Report of PCT/JP2015/079477 dated Dec. 15, 2015.

* cited by examiner

MAGNETIC RESONANCE IMAGING APPARATUS AND QUANTITATIVE MAGNETIC SUSCEPTIBILITY MAPPING METHOD

TECHNICAL FIELD

The present invention relates to a magnetic resonance imaging (MRI) technique. More particularly, it relates to an image processing technique that utilizes an acquired image to calculate a magnetic susceptibility distribution within a living body.

BACKGROUND ART

A magnetic resonance imaging apparatus is a medical-use diagnostic noninvasive imaging apparatus, utilizing nuclear magnetic resonance phenomenon, which is a phenomenon that hydrogen nucleus (protons) placed in a static magnetic field are resonant with an RF magnetic field at a specific frequency. Since nuclear magnetic resonance signals are changed depending on various physical properties, such as proton density and relaxation time, an image obtained by the MRI can depict various biological information, such as a structure or a composition of living tissues and cell properties.

In recent years, a magnetic susceptibility difference between living tissues receives attention, as one of the physical properties being measurable by the MRI. The magnetic susceptibility is a physical property that represents a degree of magnetic polarization (magnetization) of materials in the static magnetic field. In a living body, there are contained paramagnetic substances such as deoxyhemoglobin in venous blood and iron protein, and diamagnetic substances such as water constituting a large part of the living tissues and calcium serving as a basis of calcification. Creating an image quantitatively from a difference in magnetic susceptibility, i.e., the magnetic susceptibility difference between the living tissues, may be applicable to diagnosis of cerebral ischemia disease, prediction of radiation treatment effect against cancer, and identification of neurodegenerative disease.

A method for creating an image of the magnetic susceptibility difference between living tissues by utilizing the MRI is referred to as quantitative susceptibility mapping (QSM). The QSM is a method of calculating spatial variation in magnetic field caused by the magnetic susceptibility difference between living tissues, from phase information of an MR image being measured, and obtaining a magnetic susceptibility distribution according to a relational expression between the magnetic field and the magnetic susceptibility.

However, a distribution of the magnetic field is obtained by subjecting the magnetic susceptibility distribution to spatial convolution integral. Therefore, obtaining the magnetic susceptibility distribution from the magnetic field distribution is an inverse problem of the convolution integral, and thus a unique solution cannot be obtained.

In general, the least-square method is employed to obtain the magnetic susceptibility distribution from the magnetic field distribution. In this case, an error function is introduced, and a value that minimizes this error function is obtained as a solution. Representative examples of this method are, for example, TKD (Truncated-based K-space Division) (e.g., see Non Patent Document 1), Iterative SWIM (Susceptibility Weighted Imaging and Mapping) (e.g., see Non Patent Document 2 and Patent Document 1), and MEDI (Morphology enabled dipole inversion) method (e.g., see Non Patent Document 3 and Patent Document 2). Here, the TKD is a method of calculating a magnetic susceptibility distribution according to operations on k-space of the magnetic field distribution and of the point dipole magnetic field; the iterative SWIM is a method of merging through an iterative operation, the magnetic susceptibility distribution calculated according to the TKD method, with the magnetic susceptibility distribution where a fine structure is extracted according to thresholding; and the MEDI is a method that utilizes the regularized least-square method.

PRIOR ART DOCUMENT

Patent Document

Patent Document 1:
U.S. Unexamined Patent Application Publication No. 2011/0262017, SPECIFICATION
Patent Document 2:
U.S. Unexamined Patent Application Publication No. 2011/0044524, SPECIFICATION

Non Patent Document

Non Patent Document 1:
Shmueli K, et al., "Magnetic Susceptibility Mapping of Brain Tissue In Vivo Using MRI Phase Data", Magnetic Resonance in Medicine, 2009, Vol. 62, pp. 1510 to 1522
Non Patent Document 2:
Tang J, et al., "Improving Susceptibility Mapping Using a Threshold-Based K-Space/Image Domain Iterative Reconstruction Approach", Magnetic Resonance in Medicine, 2013, Vol. 69, pp. 1396 to 1407
Non Patent Document 3:
Liu T, et al., "Morphology enabled dipole inversion (MEDI) from a single-angle acquisition: comparison with COSMOS in human brain imaging", Magnetic Resonance in Medicine, 2011, Vol. 66, pp. 777 to 783

DISCLOSURE OF THE INVENTION

Problems to be Solved by the Invention

In the TKD method, a region for which inverse calculations cannot be performed is truncated at zero or at an optional value. Therefore, the TKD method has an advantage being simple and short in calculation time, but there are problems that artifacts may occur, and accuracy in the calculated magnetic susceptibility may be reduced, due to the truncation in the vicinity of a magic angle region.

The iterative SWIM method applies a masking process allowing the fine structure to be maintained, to the magnetic susceptibility distribution obtained by the TKD method, and iterates the process for updating the magnetic susceptibility distribution. This method allows the magnetic susceptibility distribution to be calculated with keeping the fine structure, but there is a problem that artifacts cannot be removed completely. In order to extract the fine structure, various thresholding processes are required. Therefore, there is a problem that if there are not provided thresholds appropriate for subjects respectively, the fine structure cannot be extracted properly.

The MEDI method calculates the magnetic susceptibility distribution, by minimizing through the iterative operation, a term that provides a smoothing effect, referred to as a regularization term, assuming a relational expression between the magnetic field and the magnetic susceptibility as a constraint. This regularized least-square method is a process that truncates a value of the signal with the magnitude corresponding to a value of a regularization parameter. Therefore, it is necessary to set an adequate regularization term, according to noise that has mixed into the magnetic field distribution. Generally, since it is not possible to obtain in advance noise information mixing into the magnetic field distribution, an adequate regularization parameter is calculated from a change curve of residual which is obtained by varying the regularization parameter more than once. Therefore, in the MEDI method, enormous calculation time is required for setting the adequate regularization parameter.

The present invention has been made in view of the situations as described above, and an object of the present invention is to provide a technique that is used in calculating the magnetic susceptibility distribution with the use of MRI, for reducing artifacts and noise through a simple process, so as to improve accuracy and precision of the magnetic susceptibility distribution being calculated.

Means for Solving the Problems

According to the present invention, a magnetic field distribution is obtained via a phase image, from a complex image acquired by MRI. Smoothing process is iteratively applied to a magnetic susceptibility distribution that is calculated from the magnetic field distribution, under the constraint based on a relational expression between the magnetic field and the magnetic susceptibility. Specifically, the magnetic susceptibility distribution is calculated according to a minimization process for minimizing an error function through the iterative operation, the error function being defined by a predetermined initial magnetic susceptibility distribution and the magnetic field distribution. On this occasion, the updated magnetic susceptibility distribution calculated according to the error function during the minimizing process, is smoothed every time the updated magnetic susceptibility distribution is calculated.

Advantage of the Invention

In calculating the magnetic susceptibility distribution by using the MRI, artifacts and noise are reduced through the simple process, thereby improving accuracy and precision of the magnetic susceptibility distribution being calculated.

EMBODIMENTS FOR CARRYING OUT THE INVENTION

Figure 1:
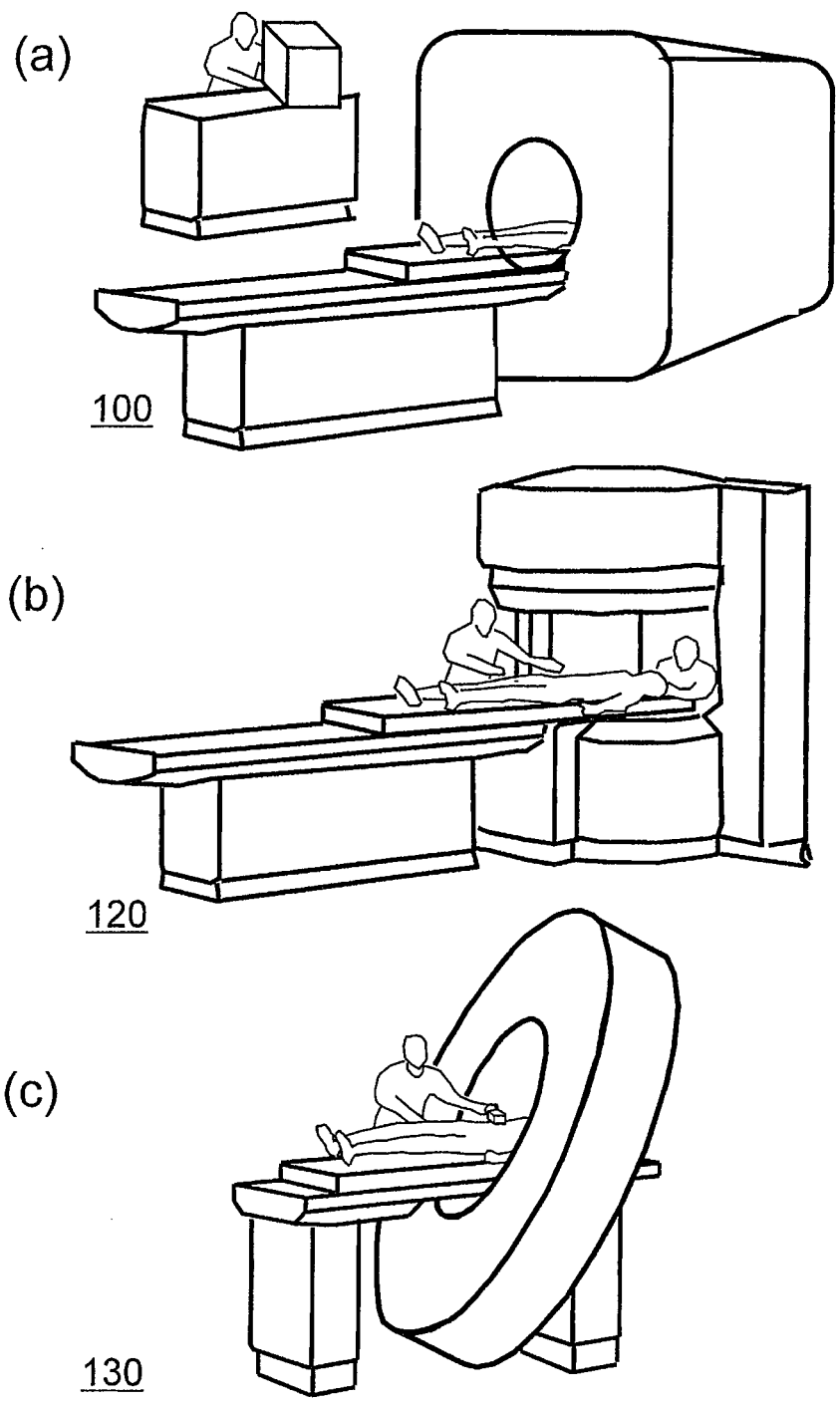
FIG. 1(a) is an external view of a vertical magnetic resonance imaging apparatus according to an embodiment of the present invention.
FIG. 1(b) is an external view of a horizontal magnetic resonance imaging apparatus according to an embodiment of the present invention.
FIG. 1(c) is an external view of the magnetic resonance imaging apparatus with enhanced sense of space according to an embodiment of the present invention.

An embodiment to which the present invention is applied will now be described. Hereinafter, in all the figures illustrating the embodiment of the present invention, elements with an identical function are labeled with the same reference numeral, unless otherwise noted, and they will not be redundantly explained. It should also be noted that the descriptions below will not limit the present invention.

[Principle in Calculating Magnetic Susceptibility Distribution]

In the present embodiment, through the use of an MRI apparatus, a complex image I at a predetermined echo time is obtained, a magnetic field distribution δ that captures changes in magnetic field caused by a magnetic susceptibility difference between living tissues, is calculated from the complex image I, and a magnetic susceptibility distribution χ is calculated from the magnetic field distribution δ. The magnetic susceptibility distribution is calculated according to so-called QSM method. Prior to describing the MRI apparatus implementing the steps above, a method of calculating the magnetic susceptibility distribution χ from the complex image I according to the QSM method will be described.

In the QSM method, a local change in magnetic field caused by the magnetic susceptibility difference between living tissues is calculated from a phase image that is obtained by the Gradient Echo(GrE) method.

When a position vector is represented as r, a relative magnetic field distribution δ(r), caused by the magnetic susceptibility difference between tissues, is expressed by the following formula 1.

[Formula 1]

$$\delta(r) = -\frac{P(r)}{\gamma \cdot B_0 \cdot TE} \qquad (1)$$

where $P(r)$ is the phase image, $\gamma$ is the nuclear gyromagnetic ratio of proton, $B_0$ is static magnetic field strength, and TE is the echo time.

The magnetic field distribution $\delta(r)$ is expressed by the following formula 2 according to Maxwell's equations concerning the static magnetic field, by using the magnetic susceptibility distribution $\chi(r)$ within a living body.

[Formula 2]

$$\delta(r) = \frac{1}{4\pi}\int \chi(r')\frac{3\cos^2\alpha - 1}{|r'-r|} \qquad (2)$$
$$= d(r) \otimes \chi(r)$$

where α is an angle formed by the vector(r'−r) with the direction of static magnetic field, and d(r) is the point-dipole magnetic field.

As shown by the formula 2, the magnetic field distribution δ(r) is represented by the convolution integral between the magnetic susceptibility distribution χ(r) and the point-dipole magnetic field d(r). Therefore, Fourier transform is applied to both sides of the formula 2, whereby the formula 2 is transformed to the following formula 3.

[Formula 3]

$$\Delta(k) = \left(\frac{1}{3} - \frac{k_z^2}{k_x^2 + k_y^2 + k_z^2}\right) \cdot X(k) \qquad (3)$$
$$= D(k) \cdot X(k)$$

where $k=(k_x, k_y, k_z)$ represents position vectors in the k-space, $\Delta(k)$, $X(k)$, and $D(k)$ are Fourier components, respectively, of the magnetic field distribution δ(r), the magnetic susceptibility distribution χ(r), and the point-dipole magnetic field d(r).

As indicated by the formula 3, the Fourier component X(k) of the magnetic susceptibility distribution can be calculated by dividing the Fourier component Δ(k) of the magnetic field distribution, by the Fourier component D(k) of the point-dipole magnetic field. However, according to the formula 3, since the reciprocals diverge in a domain in the vicinity of D(k)=0, it is not possible to calculate X(k) straightforwardly.

The domain where D(k)=0 is referred to as the magic angle, forming a region of reverse bicone with the apex nearly double the angle of 54.7° with respect to the magnetic field direction. Due to this magic angle, the QSM method which calculates the magnetic susceptibility distribution from the magnetic field distribution comes down to an ill-conditioned inverse problem.

As a representative method for solving this problem, the TKD method, the Iterative SWIM method (hereinafter, simply referred to as "SWIM method"), and the MEDI method are provided as described above.

In the TKD method, the reciprocal of Fourier component D(k) of the point-dipole magnetic field d(r) is obtained, and the vicinity of the magic angle region thereof is truncated at zero or at any value. Thereafter, the obtained value is multiplied by the Fourier component Δ(k) of the measured magnetic field distribution δ(r), and the product is subjected to the inverse Fourier transform to the real space data, thereby calculating the magnetic susceptibility distribution χ(r).

In the Iterative SWIM method, thresholding is applied to the magnetic susceptibility distribution calculated by a method such as the TKD method, and only a fine structure is extracted. Next, the magnetic susceptibility distribution of the fine structure is calculated, which is obtained by masking a part of the magnetic susceptibility other than the fine structure. The original magnetic susceptibility distribution and the magnetic susceptibility distribution of the fine structure are mixed in the k-space, thereby calculating a modified magnetic susceptibility distribution. Thresholding is applied to the modified magnetic susceptibility distribution, and then, the fine structure is extracted again. By repeating a series of those processes above, the magnetic susceptibility distribution is calculated.

In the MEDI method, as shown by the following formula 4, assuming the relational expression between the magnetic field and the magnetic susceptibility, as a constraint, the term referred to as regularization term which provides a smoothing effect, is minimized through the iterative operation, thereby calculating the magnetic susceptibility distribution χ(r).

[Formula 4]

$$\chi(r) = \underset{\chi}{\mathrm{argmin}} \|W(\delta - F_D\chi)\|_2^2 + \lambda\|M\nabla\chi\|_1 \qquad (4)$$

where χ is the magnetic susceptibility distribution vector to be calculated, δ is the magnetic field distribution vector calculated from the phase image, W is the matrix having a weight vector as a diagonal component which is calculated based on an absolute value image, M is the matrix having a binary edge mask vector as the diagonal component, assuming the edge region as 0 and the other area as 1 on the basis of space gradient of the absolute value image. $F_D$ is an operator representing the convolution integral, ∇(nabla) is a three-dimensional space-gradient operator, $\|a\|_n$ is Ln norm of any vector a. The second term λ in the formula 4 is a regularization parameter for striking a balance between the smoothing effect and accuracy of the magnetic susceptibility.

As shown in the formula 4, the MEDI method uses as the regularization term, L1 norm of the vector obtained by multiplying Total Variation (TV) $\nabla_\chi$ of the magnetic susceptibility distribution in the course of calculation, by the edge mask M which is based on the absolute value image. In general, a least-square solution with L1 norm regularization of any vector a, is likely to be a sparse solution. Therefore, according to the MEDI method, a region with less variation in the absolute value image is smoothed, resulting in that the magnetic susceptibility distribution that retains the edge region with a major change is obtained.

It should be understood that the regularized least-square method including the MEDI method is a process for truncating a signal value with a magnitude that corresponds to a value of the regularization parameter. Therefore, if the regularization parameter is too large, the fine structure is also likely to be eliminated along with noise, and further reducing the magnetic susceptibility of the entire image, resulting in that the calculated magnetic susceptibility is deteriorated. On the other hand, if the regularization parameter is too small, noise is likely to be increased, even though the fine structure and the magnetic susceptibility of the entire image are maintained.

Therefore, in the MEDI method, it is necessary to provide an adequate regularization parameter. In the case where the adequate regularization parameter is provided, a standard deviation of a residual of the first term in the formula 4 becomes equal to the standard deviation of the noise that is mixed into the measured magnetic field distribution. In general, however, since it is not possible to obtain in advance, information of the noise mixed into the magnetic field distribution, the regularization parameter is made to vary more than once to calculate residuals, and the adequate regularization parameter is obtained according to a change curve of the residuals thus calculated. Accordingly, the MEDI method requires enormous calculation time for providing the adequate regularization parameter.

In the present embodiment, considering the aforementioned publicly-known methods, an MRI apparatus and QSM method are provided in calculating the magnetic susceptibility distribution by using MRI, so as to obtain highly accurate and highly precise magnetic susceptibility distribution, according to a simple process along with reducing artifacts and noise.

[External View of MRI Apparatus]

Firstly, an magnetic resonance imaging apparatus (MRI apparatus) of the present embodiment will be described. FIGS. 1(a) to 1(c) are external views showing the MRI apparatus according to the present embodiment. FIG. 1(a) illustrates the MRI apparatus of the horizontal magnetic field type 100 which uses a tunnel-type magnet for generating a static magnetic field by a solenoid coil. FIG. 1(b) illustrates the MRI apparatus 120 of a hamburger-type (open-type) vertical magnetic field system in which the magnets are separated vertically so as to enhance a sense of openness. FIG. 1(c) illustrates the MRI apparatus 130 of the same tunnel-type as FIG. 1(a), using a magnet with reduced depth and put in a slanting position, thereby enhancing the sense of openness more.

The present embodiment may employ any types of the MRI apparatus having those external views as shown above.

It should be noted that these are a few examples, and the MRI apparatus of the present embodiment is not limited to those examples shown here. In the present embodiment, various publicly-known MRI apparatuses may be employed, including any mode or any type thereof.

The MRI apparatus 100 will now be described as a representative example, unless otherwise distinguished. The present embodiment employs, for example, a coordinate system assuming a direction of the static magnetic field of the MRI apparatus 100 as z-direction, and two other directions vertical to the z-direction as x-direction and y-direction; i.e., the direction parallel to a bed surface where a subject to be measured is placed is the x-direction and the other direction is the y-direction. It should also be noted that the static magnetic field will be simply referred to as magnetic field in the following.

[Functional Configuration of MRI Apparatus]

Figure 2:
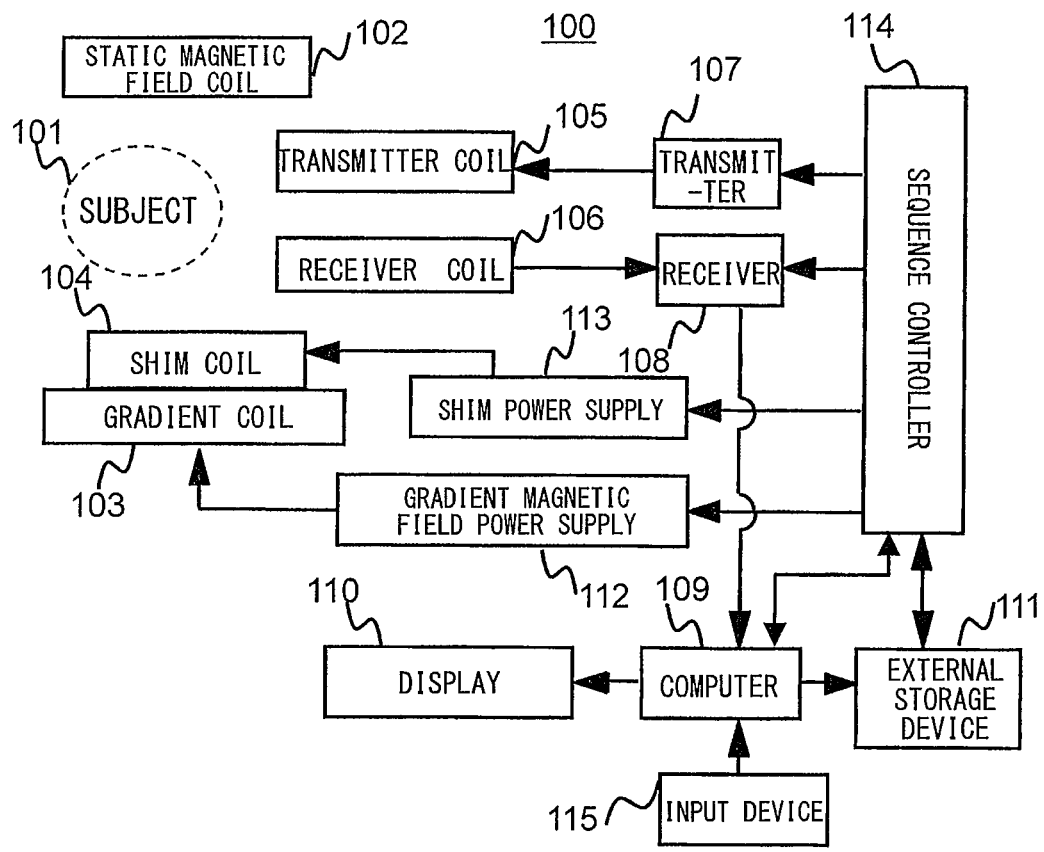
FIG. 2 is a block diagram showing a schematic configuration of the MRI apparatus according to an embodiment of the present invention.

FIG. 2 is a functional block diagram of the MRI apparatus 100. As illustrated, the MRI apparatus 100 of the present embodiment is provided with a static magnetic field coil 102 comprising a static magnetic field coil and a static magnetic field generation magnet, configured to generate a static magnetic field in the space where a subject 101 is placed, a shim coil 104 for adjusting a static magnetic field distribution, a transmitter RF coil 105 (hereinafter, simply referred to as "transmitter coil") for transmitting an RF magnetic field to a measurement region of the subject 101, a receiver RF coil 106 (hereinafter, simply referred to as "receiver coil") for receiving nuclear magnetic resonance signals generated from the subject 101, a gradient coil 103 for applying a gradient magnetic field to each of the directions; the x-direction, the y-direction, and the z-direction, so as to add positional information to the nuclear magnetic resonance signals generated from the subject 101, a transmitter 107, a receiver 108, a computer 109, a gradient magnetic field power supply 112, a shim power supply 113, and a sequence controller 114.

Various types of the static magnetic field coil 102 may be employed, depending on the structures of the MRI apparatuses 100, 120, and 130 as shown in FIGS. 1(a), 1(b), and 1(c), respectively. The gradient coil 103 and the shim coil 104 are driven by the gradient magnetic field power supply 112 and the shim power supply 113, respectively. In the present embodiment, there will be described the case where the transmitter coil 105 and the receiver coil 106 separately provided, are used, for instance. However, it is possible to configure such that one coil is employed, which serves both functions, the transmitter coil 105 and the receiver coil 106. The RF magnetic field applied from the transmitter coil 105 is generated by the transmitter 107. Nuclear magnetic resonance signals detected by the receiver coil 106 are transmitted to the computer 109 via the receiver 108.

The sequence controller 114 controls operations of the gradient magnetic field power supply 112 being a power source for driving the gradient coil 103, the shim power supply 113 being a power source for driving the shim coil 104, the transmitter 107, and the receiver 108, thereby controlling application of the gradient magnetic field and the RF magnetic field, and receiving timing of the nuclear magnetic resonance signal. A time chart of the control is referred to as a pulse sequence, whose settings are previously configured depending on the measurement, and it is stored, for example, in a storage device being provided in the computer 109 as described below.

The computer 109 controls the entire operation of the MRI apparatus 100, along with performing various computations on the nuclear magnetic resonance signals being received. In the present embodiment, the computer generates a complex image of at least one echo time, a phase image, a magnetic field distribution, a magnetic susceptibility distribution, and the like. The computer 109 is an information processor including a CPU, a memory, and a storage device, and the computer 109 is connected to a display 110, an external storage device 111, and an input device 115.

The display 110 is an interface for an operator, configured to display information such as a result obtained by computations. The input device 115 is an interface configured to allow the operator to input conditions, parameters, and the like, necessary for the computations performed in the present embodiment. The input device 115 of the present embodiment allows the user to input measurement parameters, such as the number of echoes to be measured, a reference echo time, and an echo interval. The external storage device 111, along with the storage device, holds data such as the data used in various computations executed by the computer 109, data obtained through the computations, conditions and parameters being inputted.

[Functional Block of the Computer]

As described above, in the present embodiment, under the constraint based on the relational expression between the magnetic field magnetic field and the magnetic susceptibility, a smoothing process is performed through the iterative operation, thereby calculating the magnetic susceptibility distribution, easily with a high degree of precision. Next, a description will be provided regarding a functional configuration of the computer 109 for implementing the aforementioned functions.

Figure 3:
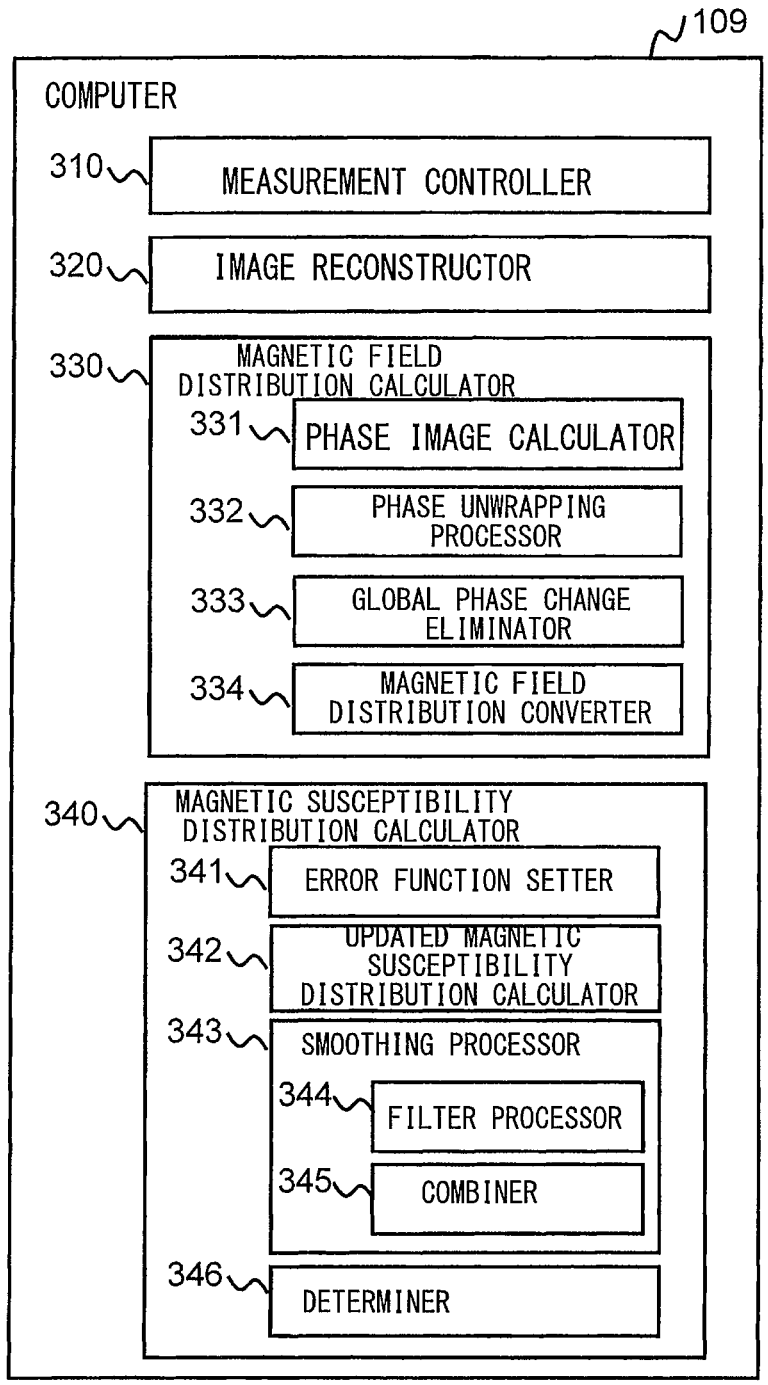
FIG. 3 is a functional block diagram of a computer according to an embodiment of the present invention.

FIG. 3 is a functional block diagram showing the computer 109 according to the present embodiment. The computer 109 of the present embodiment is provided with, a measurement controller 310 configured to measure complex signals of nuclear magnetic resonance signals (echo signals) generated from the subject, in response to irradiation of RF magnetic field pulses, an image reconstructor 320 configured to reconstruct a complex image where a pixel value is a complex value, from the complex signals measured by the measurement controller 310, a magnetic field distribution calculator 330 configured to generate a phase image from the complex image reconstructed by the image reconstructor 320, and to calculate a magnetic field distribution from the phase image, and a magnetic susceptibility distribution calculator 340 configured to calculate the magnetic susceptibility distribution from the magnetic field distribution calculated by the magnetic field distribution calculator 330.

The computer 109 is provided with a CPU, a memory, and a storage device. The CPU loads programs held in advance in the storage device into the memory and executes those programs, whereby those various functions are implemented by the computer 109. The storage device or the external storage device 111 may store various data used for processing of the functions, and various data generated in process.

At least one of the various functions implemented by the computer 109 may also be implemented by an information processor that is independent of the MRI apparatus 100 and data transmittable and receivable thereto and therefrom. Furthermore, all or a part of the functions may be implemented by hardware such as ASIC (Application Specific Integrated Circuit) and FPGA (Field-Programmable Gate Array).

[Flow of QSM Process]

Figure 4:
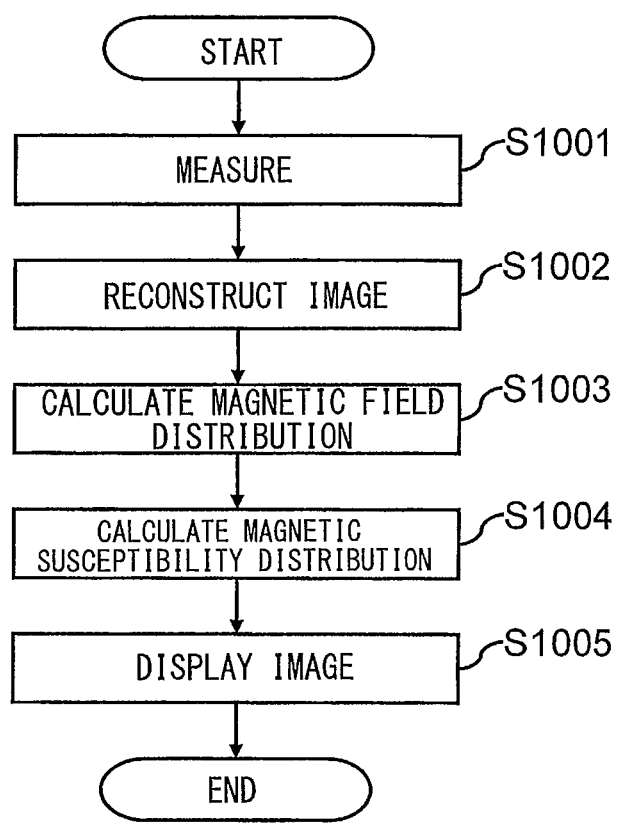
FIG. 4 is a flowchart showing QSM process according to an embodiment of the present invention.

There will be described a flow of the process according to the QSM method (QSM process) implemented by the aforementioned functions of the computer 109 of the present embodiment. FIG. 4 is a flowchart for describing the flow of the QSM process according to the present embodiment.

Firstly, the measurement controller 310 controls the sequence controller 114 according to a predetermined pulse sequence, thereby measuring an echo signal at a preset echo time (step S1001).

Then, the image reconstructor 320 places thus obtained echo signals in the k-space, applies Fourier transform thereto, thereby reconstructing a complex image I (step S1002).

The magnetic field distribution calculator 330 performs a magnetic field distribution calculating process for calculating the magnetic field distribution δ from the complex image I (step S1003).

Then, the magnetic susceptibility distribution calculator 340 performs a magnetic susceptibility distribution calculating process for calculating the magnetic susceptibility distribution χ from the magnetic field distribution δ being obtained (step S1004), and displays thus obtained magnetic susceptibility distribution χ on the display 110 (step S1005).

When the magnetic susceptibility distribution χ is displayed on the display 110, it is also possible to display an image obtained in the course of the QSM process on the display 110, if required, in addition to the magnetic field distribution δ, and the like, calculated in step S1003.

Details of each step of the QSM process according to the present embodiment will now be described.

[Measurement: S1001]

The measurement controller 310 activates the sequence controller 114, according to the pulse sequence that is configured on the basis of the parameters inputted by a user via the input device 115, and performs measurement so as to obtain a nuclear magnetic resonance signal (echo signal) at a preset echo time (TE). The sequence controller 114 controls each part of the MRI apparatus 100 according to the instructions from the measurement controller 310, so as to perform the measurement. In the present embodiment, an echo signal of at least one echo time is obtained.

An example of the pulse sequence used by the measurement controller 310 for the measurement will be described. By way of example, in the present embodiment, a pulse sequence of GrE (Gradient Echo) system may be employed. The pulse sequence of this GrE system is sensitive to local magnetic field variation generated by magnetic susceptibility differences between living tissues.

Figure 5:
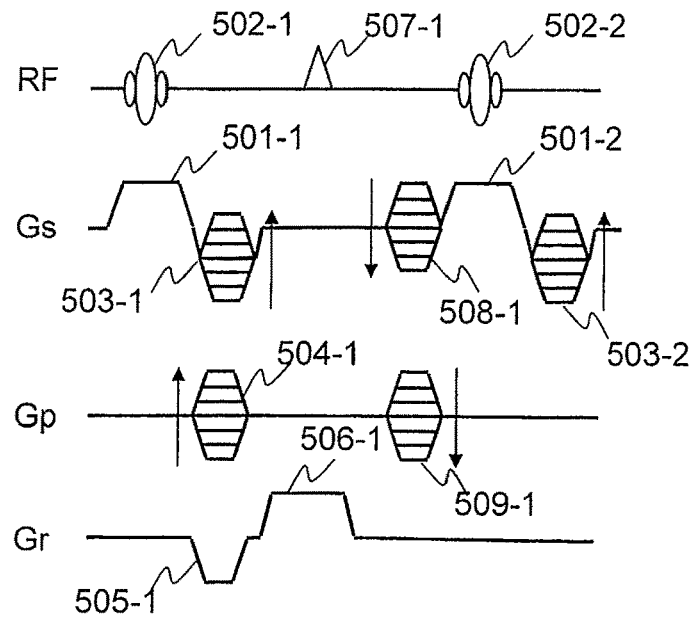
FIG. 5 illustrates a pulse sequence of RSSG (RF-spoiled-Steady-state Acquisition with Rewound Gradient-Echo) sequence.

FIG. 5 illustrates RSSG (RF-spoiled-Steady-state Acquisition with Rewound Gradient-Echo) sequence 510, as an example of the GrE-system pulse sequence. In this figure, RF, Gs, Gp, and Gr represent, respectively, an RF magnetic field, a slice gradient magnetic field, a phase encoding gradient magnetic field, and a readout gradient magnetic field.

In the RSSG sequence 510, high-frequency (RF) magnetic field pulse 502 is applied along with application of the slice gradient magnetic field pulse 501, thereby exciting magnetization of a predetermined slice within the subject 101. Then, a slice encoding gradient magnetic field pulse 503 and a phase encoding gradient magnetic field pulse 504 are applied, so as to add positional information in the slice-direction and in the phase-encoding direction, to a phase of the magnetization.

After applying a readout gradient magnetic field pulse 505 for dephasing, to disperse a phase of nuclear magnetization within a pixel, one nuclear magnetic resonance signal (echo) 507 is measured, along with applying a readout gradient magnetic field pulse 506 for adding positional information in the readout direction. And finally, a slice encoding gradient magnetic field pulse 508 and a phase encoding gradient magnetic field pulse 509 for rephasing are applied, for convergence of the phase of nuclear magnetization that has been dephased by the slice encoding gradient magnetic field pulse 503 and the phase encoding gradient magnetic field pulse 504.

The measurement controller 310 executes the procedures above, repeatedly every repetition time TR, while varying strength of the slice encoding gradient magnetic field pulses 503 and 508 (slice-encoding count ks) and of the phase encoding gradient magnetic field pulses 504 and 509 (phase-encoding count kp), and the phase of the RF pulse 502, whereby echoes necessary for acquiring one image are measured. In this situation, the phase of the RF pulse 502 may be incremented by 117 degrees, for instance. In FIG. 5, the number following the hyphen indicates the number of repetitions.

The measured echoes are arranged in three-dimensional k-space having kr, kp, and ks as coordinate axes. In this situation, one echo occupies one line which is parallel to the kr axis in the k-space. As an absolute value image obtained by this RSSG sequence 510, T1 (longitudinal relaxation time) weighted image is obtained when TE is set short, whereas T2* weighted image in which the phase dispersion within the pixel is reflected is obtained when TE is set long.

The RSSG sequence 510 is taken as an example here, which is one method of the Cartesian imaging for acquiring data in parallel to the coordinate axes of the k-space. In the present embodiment, however, any sequence may be employed to acquire data in any k-space domain.

By way of example, another sequence may be employed for acquiring plural echoes at a single TR, and arranging those echoes in various domains of k-space. Alternatively, another sequence may be employed which performs the measurement more than once, and data is obtained in different k-space domains respectively by the plural measurements, and integrates those data items to obtain one image. Further alternatively, non-Cartesian imaging may be employed, such as radial scanning to acquire data in k-space in rotational manner.

It is also possible to employ a sequence for creating one complex image and one phase image, from different complex images and phase images acquired at plural TEs. In the case where a pulse sequence that implements Dixon method for acquiring an image from plural signals that are obtained at plural TEs, the magnetic field distribution δ can be obtained in the process of separating water from fat, for instance. Therefore, in this case, a process for generating the phase image P as described in the following becomes unnecessary.

[Image Reconstruction: S1002]

Next, the image reconstruction process in the aforementioned step S1002 will be described. The image reconstructor 320 places in the k-space the echo signals at the echo time measured in step S1001, and applies Fourier transform to the echo signals. Then, image reconstructor 320 calculates the complex image I where each pixel is a complex number.

[Magnetic Field Distribution Calculating Process: S1003]

Next, there will be described the magnetic field distribution calculating process in the aforementioned step S1003, according to the magnetic field distribution calculator 330. The magnetic field distribution calculator 330 of the present embodiment calculates the magnetic field distribution δ from the complex image I that is reconstructed by the image reconstructor 320. The magnetic field distribution δ being calculated captures local variation of the magnetic field, caused by the magnetic susceptibility differences between living tissues.

The magnetic field distribution calculator 330 firstly calculates the phase image P from the complex image I, and applies various phase image processing to thus calculated phase image P, so as to remove background phase. Then, the magnetic field distribution δ is obtained from the phase image P after performing such phase image processing.

In the phase image processing, a phase component originated from the magnetic susceptibility is extracted, by removing the phase component originated from any element other than the magnetic susceptibility. Specifically, in the calculated phase image P, there are performed a phase unwrapping process for removing a phase exceeding the range from $-\pi$ to $\pi$ and folded back, and a global phase change eliminating process for eliminating global phase change caused by a biological form.

In order to implement the processes above, the magnetic field distribution calculator 330 of the present embodiment is provided with, as shown in FIG. 3, a phase image calculator 331 configured to calculate the phase image P from the complex image I, a phase unwrapping processor 332 configured to perform the phase unwrapping process, a global phase change eliminator 333 configured to perform the global phase change eliminating process, and a magnetic field distribution converter 334 configured to convert the phase image P after the phase processing into the magnetic field distribution δ.

The phase image calculator 331 obtains as a pixel value, an argument of each pixel value of the complex image I, so as to calculate the phase image P. In other words, the phase image P is an image having pixel values, which are phase components in the complex numbers of the pixels in the complex image I. Here, the pixel value P(r) of the phase image P at the pixel r is calculated according to the formula 5, by using the pixel value I(r) of the complex image I:

$$P(r)=\arg\{I(r)\} \quad (5)$$

The phase unwrapping processor 332 executes the phase unwrapping process on the phase image P, for eliminating the phase exceeding the range from $-\pi$ to $\pi$ and folded back. In a partial region of the phase image P, the phase value exceeding the range from $-\pi$ to $\pi$ is folded back into the range from $-\pi$ to $\pi$. Therefore, in order to obtain an accurate phase in the entire portion to be imaged (e.g., a head), it is necessary to correct this folding back. In the present embodiment, by using an region growing method, for instance, a phase value folded back into the range from $-\pi$ to $\pi$ is corrected.

The global phase change eliminator 333 eliminates a global phase change that occurs due to the biological form, in the phase image P after the phase unwrapping process is performed.

Each pixel value of the phase image P is a sum of the global phase change caused by static magnetic field inhomogeneity that may occur depending on forms of the portion to be imaged, or the like, and a local phase change caused by the magnetic susceptibility change between tissues. The global phase change and the local phase change are associated with, respectively, a low-frequency component and a high-frequency component in the k-space of the phase image P. According to this process, only the global phase change is eliminated, and the local phase change caused by the magnetic susceptibility change between tissues can be extracted.

The global phase change eliminator 333 of the present embodiment performs as the global phase change eliminating process, firstly applies a low-pass filter process to every two-dimensional image of the three-dimensional image (original image) being obtained, and calculates a low resolution image. Then, the original image is subjected to complex division by the low resolution image. Accordingly, the global phase change included in the low resolution image is eliminated from the original image.

There are various methods for eliminating the global phase change. There is one method, by way of example, that extracts the global phase change by performing a fitting on a three-dimensional image according to a low-order polynomial expression, and subtracts the global phase change from the original image. In eliminating the global phase change, this kind of different methods may be applicable.

It should be noted that the phase unwrapping process and the global phase change eliminating process of the phase image processing are just examples, and they are not limited to those examples. Any one of those two processes may be omitted. Those processes may be performed in any order. Neither of those two processes may be performed.

The magnetic field distribution converter 334 utilizes the formula 1, to convert the phase image P after the phase image processing is performed, into the magnetic field distribution δ.

[Flow of Magnetic Field Distribution Calculating Process]

Figure 6:
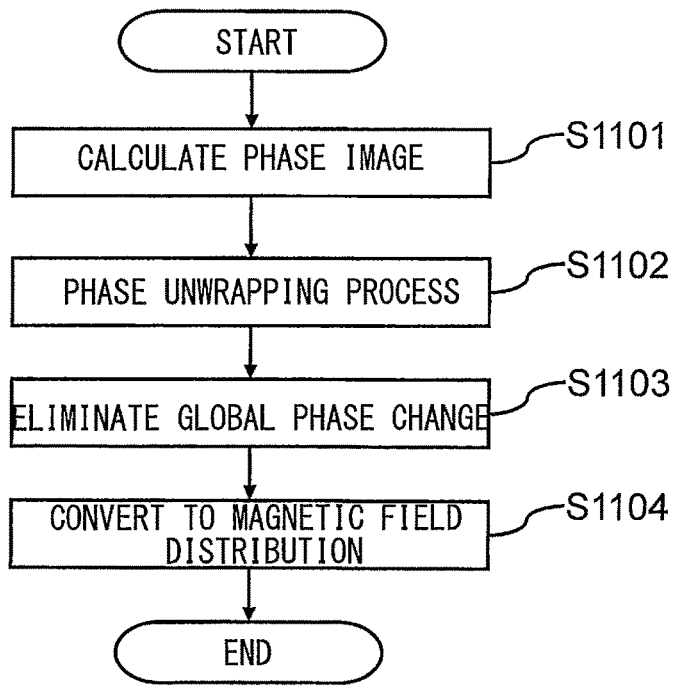
FIG. 6 is a flowchart of a process for calculating a magnetic field distribution according to an embodiment of the present invention.

There will be described one example of the magnetic field distribution calculating process flow, according to the functions of the magnetic field distribution calculator 330 of the present embodiment. FIG. 6 is a flowchart of the magnetic field distribution calculating process of the present embodiment.

The phase image calculator 331 calculates the phase image P from the complex image I (step S1101).

Then, the magnetic field distribution calculator 330 performs various phase image processing on the phase image P, thereby obtaining a phase image after the phase processing. In the present embodiment, for example, the phase unwrapping processor 332 performs the phase unwrapping process on the phase image P being calculated (step S1102), and the global phase change eliminator 333 performs the global phase change eliminating process on the phase image P after the phase unwrapping process is performed (step S1103). As described above, the phase image processing may be performed in any order. Only one of the phase image processes may be performed, or neither of them may be performed. Furthermore, the present embodiment is not limited to those example as discussed above.

Lastly, the magnetic field distribution converter 334 converts the phase image after the phase image processing, into the magnetic field distribution (step S1104), and the process ends.

[Magnetic Susceptibility Distribution Calculating Process: S1004]

Next, there will be described the magnetic susceptibility distribution calculating process of the aforementioned step S1004, according to the magnetic susceptibility distribution calculator 340. The magnetic susceptibility distribution calculator 340 of the present embodiment utilizes the magnetic field distribution $\delta$ calculated by the magnetic field distribution calculator 330, so as to obtain the magnetic susceptibility distribution $\chi$.

The magnetic susceptibility distribution calculator 340 performs a minimization process that minimizes an error function through an iterative operation, the error function being defined by a predetermined initial magnetic susceptibility distribution $\chi_0$ and the magnetic field distribution $\delta$, thereby calculating the magnetic susceptibility distribution $\chi$. In this situation, the updated magnetic susceptibility distribution $\chi_{UPD}$ calculated according to the error function, during the minimization process, is smoothed every time the updated magnetic susceptibility distribution is calculated. It should be noted that the updated magnetic susceptibility distribution $\chi_{UPD}$ is obtained by updating the initial magnetic susceptibility distribution $\chi_0$, on the basis of the error function.

In order to implement those as described above, the magnetic susceptibility distribution calculator 340 of the present embodiment is provided with an error function setter 341 configured to set the error function, an updated magnetic susceptibility distribution calculator 342 configured to calculate the updated magnetic susceptibility distribution $\chi_{UPD}$ from the magnetic field distribution $\delta$ and initial magnetic susceptibility distribution $\chi_0$, by using the error function being set, a smoothing processor 343 configured to smooth the updated magnetic susceptibility distribution $\chi_{UPD}$, and to generate a combined magnetic susceptibility distribution $\chi_{ADD}$, and a determiner 346 configured to determine the end of the iterative operation, along with updating the initial magnetic susceptibility distribution $\chi_0$ to the combined magnetic susceptibility distribution $\chi_{ADD}$ being calculated.

The smoothing processor 343 is provided with, a filter processor 344 configured to generate the magnetic susceptibility distribution after the filter process is performed (processed magnetic susceptibility distribution) $\chi_{SMT}$, by applying a predetermined smoothing filter to the updated magnetic susceptibility distribution $\chi_{UPD}$, and a combiner 345 configured to combine the updated magnetic susceptibility distribution $\chi_{UPD}$ and the processed magnetic susceptibility distribution $\chi_{SMT}$, so as to generate the combined magnetic susceptibility distribution $\chi_{ADD}$.

[Error Function Setter]

As shown in the formula 2, the magnetic field distribution $\delta$ is obtained by applying the spatial convolution integral to the magnetic susceptibility distribution $\chi$. If the formula 2 is expressed using vectors and matrix, intended for all the pixels within the phase image P, the magnetic field distribution is expressed as the following formula 6.

$$\delta = F_D \chi \quad (6)$$

where $\delta$ is the column vector of the magnetic field distribution having the magnitude of the entire pixel count N, and $\chi$ is the column vector of the magnetic susceptibility distribution to be calculated, and $F_D$ is the matrix having the magnitude of N×N, corresponding to the convolution operation applied to the magnetic susceptibility distribution $\chi$.

The updated magnetic susceptibility distribution calculator 342 of the present embodiment obtains the magnetic susceptibility distribution $\chi$ from the formula 6, according to the least-square method. In this situation, the error function is introduced and minimized, whereby a solution is obtained.

The error function setter 341 of the present embodiment sets the error function that is used when the updated magnetic susceptibility distribution calculator 342 calculates the updated magnetic susceptibility distribution. The error function $e(\chi_0)$ being provided may be expressed by the following formula 7, for instance.

[Formula 7]

$$e(\chi_0) = \|W(\delta - F_D \chi_0)\|_2^2 \quad (7)$$

where W is the matrix having the weight vector (hereinafter, referred to as "weight W") as the diagonal component calculated on the basis of the phase value component of the complex image I, and $F_D$ is the operator representing the convolution integral, and $\|a\|_2^2$ represents squares of L2 norm (Euclidean norm) of optional vector a.

In other words, the error function is provided by assigning the weight W to the function defined by the magnetic field distribution $\delta$ and a result of the convolution operation performed on the initial magnetic susceptibility distribution $\chi_0$. This weight W is calculated on the basis of the phase value component (phase image P) of the complex image as discussed above.

Specifically, the error function setter 341 calculates phase fluctuation of each pixel from the phase image P, and further calculates the weight W according to the magnitude of thus obtained phase fluctuation. By way of example, the calculation is made in such a manner that the larger is the phase fluctuation, the smaller becomes the weight W.

A statistical indicator such as standard deviation may be employed to represent the phase fluctuation, for example, calculated by using plural pixel values (phase values) in the region around the pixel targeted for calculating the phase fluctuation.

It should be noted that the phase image P to be used may be the one obtained from the complex image I, or the one obtained after performing the aforementioned various phase image processing on the phase image P obtained from the complex image I.

[Updated Magnetic Susceptibility Calculator]

As discussed above, the updated magnetic susceptibility distribution calculator 342 uses the error function $e(\chi_0)$ to calculate the updated magnetic susceptibility distribution $\chi_{UPD}$ from the initial magnetic susceptibility distribution $\chi_0$. In this example here, the updated magnetic susceptibility distribution calculator 342 calculates the gradient $\nabla e(\chi_0)$ of the error function $e(\chi_0)$, and calculates the updated magnetic susceptibility distribution $\chi_{UPD}$ according to the following formula 8, by using thus calculated gradient $\nabla e(\chi_0)$:

$$\chi_{UPD} = \chi_0 + \nabla e(\chi_0) \quad (8)$$

In the present embodiment, the initial magnetic susceptibility distribution $\chi_0$ which is initially provided may be optional. By way of example, a distribution with all the values set to zero may be the initial magnetic susceptibility distribution $\chi_0$.

[Smoothing Processor; Filter Processor]

The smoothing processor 343 performs smoothing by applying the smoothing filter to the updated magnetic susceptibility distribution $\chi_{UPD}$, thereby obtaining the processed magnetic susceptibility distribution $\chi_{SMT}$. In this process, the filter processor 344 employs an edge preserving smoothing filter as the smoothing filter, and performs a linear smoothing process adaptively to local magnetic susceptibility fluctuation of each pixel value in the updated magnetic susceptibility distribution $\chi_{UPD}$.

Specifically, assuming an optional pixel position in the updated magnetic susceptibility distribution $\chi_{UPD}$ is r, an average value in the local region n×n (n is an integer at least one) around the position is $\mu(r)$, and dispersion is $\sigma(r)^2$, the pixel value $\chi_{SMT}(r)$ of the processed magnetic susceptibility distribution $\chi_{SMT}$ being the magnetic susceptibility distribution after applying the edge preserving smoothing filter at the position r, is expressed by the following formula 9:

[Formula 9]

$$\chi_{SMT}(r) = \mu(r) + \frac{\sigma(r)^2 - v^2}{\sigma(r)^2}(\chi_{UPD}(r) - \mu(r)) \quad (9)$$

where $v^2$ is the parameter corresponding to noise dispersion mixed into the magnetic susceptibility distribution $\chi$. In the present embodiment, there is employed as the parameter, an average value of the local dispersion $\sigma(r)^2$ at each pixel in the updated magnetic susceptibility distribution $\chi_{UPD}$.

According to the edge preserving smoothing filter which is applied in the present embodiment, as indicated by the formula 9, smoothing acts strongly on the region where local dispersion is small, yielding a value close to the local average value, and thus a quantitative value of the magnetic susceptibility can be maintained. On the other hand, the region where the local dispersion is large, the smoothing acts weakly, preserving an edge portion that includes a fine structure. Therefore, by applying this edge preserving smoothing filter to the updated magnetic susceptibility distribution $\chi_{UPD}$, noise in the magnetic susceptibility distribution is reduced, and an edge between fine veins and between tissues with large magnetic susceptibility fluctuation is automatically extracted and preserved.

In the present embodiment, the aforementioned edge preserving smoothing filter is employed, but a filter used in the smoothing process is not limited to this example. By way of example, a publicly-known edge preserving smoothing filter, such as a median filter and a bilateral filter, may be employed.

[Smoothing Processor; Combiner]

The combiner 345 merges the updated magnetic susceptibility distribution $\chi_{UPD}$ with the processed magnetic susceptibility distribution $\chi_{SMT}$, thereby calculating the combined magnetic susceptibility distribution $\chi_{ADD}$. Merging is performed so that increase of noise is prevented along with maintaining the fine structure of the magnetic susceptibility distribution. By way of example, merging is performed in such a manner that the Fourier component of the processed magnetic susceptibility distribution $\chi_{SMT}$ to which the edge preserve smoothing has been applied, is inserted into the vicinity of the magic angle in the k-space that is susceptible to noise.

The combiner 345 converts the updated magnetic susceptibility distribution $\chi_{UPD}$ and the processed magnetic susceptibility distribution $\chi_{SMT}$ into the k-space data, the k-space data items obtained after the conversion are respectively weighted, and are added together, thereby obtaining the combined magnetic susceptibility distribution $\chi_{ADD}$.

Specifically, the combiner 345 firstly converts the updated magnetic susceptibility distribution $\chi_{UPD}$ and the processed magnetic susceptibility distribution $\chi_{SMT}$, respectively, into k-space data, according to Fourier transform. Then, each k-space data item (Fourier component) after conversion is weighted so as to achieve the objective as described above, and thus weighted k-space data items are added together. After the addition is performed, the combined magnetic susceptibility distribution $\chi_{ADD}$ is obtained according to inverse Fourier transform.

Weighting in the k-space may be performed by creating a weighted image G and multiplying the k-space data by the weighted image G. At this time, in the weighted image $G_{UPD}$ by which the k-space data obtained from the updated magnetic susceptibility distribution $\chi_{UPD}$ is multiplied, for example, the weight assigned to the data in the vicinity of the magic angle region may be set smaller than the weight assigned to another region. On the other hand, in the weighted image $G_{SMT}$ by which k-space data obtained from the processed magnetic susceptibility distribution $\chi_{SMT}$ is multiplied, the weight assigned to the data in the vicinity of the magic angle region is set larger than the weight assigned to the data in another region.

This is because the updated magnetic susceptibility distribution $\chi_{UPD}$ has relatively large amount of noise, and it is necessary to reduce contribution of data in the vicinity of the magic angle region, so as to prevent increase of noise. On the other hand, noise has been reduced in the processed magnetic susceptibility distribution $\chi_{SMT}$, and therefore, data contribution in the vicinity of the magic angle region is increased so as to maintain the fine structure.

As the weighted images $G_{UPD}(k)$ and $G_{SMT}(k)$ that satisfy those conditions above, weighted images defined by the following formula 10 may be employed, for instance, by using the Fourier component D(k) of the point-dipole magnetic field and an adjustment parameter b for adjusting the magnitude of the magic angle region. It should be noted that k indicates data position in the k-space.

[Formula 10]

$$G_{UPD}(k) = \begin{cases} 1 & \text{if } |D(k)| \geq b \\ |D(k)|/b & \text{if } |D(k)| < b \end{cases} \quad (10)$$

$$G_{SMT}(k) = 1 - G_{UPD}(k)$$

In the aforementioned formula 10, a region where the Fourier component value is smaller than the predetermined value (b) is assumed as the magic angle region in the updated magnetic susceptibility distribution $\chi_{UPD}$.

In the case where the adjustment parameter b is 0, $G_{UPD}(k)$ becomes 1 and $G_{SMT}(k)$ becomes 0. Accordingly, this is a simple least-square method which minimizes the error function of the formula 6 without performing the edge preserving smoothing process.

[Determiner]

The determiner 346 determines the end of the iterative operation in the minimizing process for minimizing the error function $e(\chi_0)$ through the iterative operation. When it is determined that the process continues, that is, iteration of the operation is determined, the latest combined magnetic susceptibility distribution $\chi_{ADD}$ at that timing is set as the initial magnetic susceptibility distribution $\chi_0$, thereby updating the initial magnetic susceptibility distribution $\chi_0$. When the end of the operation is determined, the latest combined magnetic susceptibility distribution $\chi_{ADD}$ at that timing is outputted as the magnetic susceptibility distribution.

In the present embodiment, when the updated magnetic susceptibility distribution $\chi_{UPD}$ is calculated, the determiner 346 uses this updated magnetic susceptibility distribution $\chi_{UPD}$ and the initial magnetic susceptibility distribution $\chi_0$ at that point of time, to determine if it is the end of the operation. The determiner 346 utilizes an evaluation function $f(\chi_{UPD})$ expressed by the following formula 11, for instance, and when its value is smaller than a predetermined threshold $\varepsilon$, the end of the operation is determined.

[Formula 11]

$$f(\chi_{UPD}) = \frac{\|\chi_{UPD} - \chi_0\|_2}{\|\chi_0\|_2} < \varepsilon \qquad (11)$$

[Flow of the Magnetic Susceptibility Distribution Calculating Process]

Figure 7:
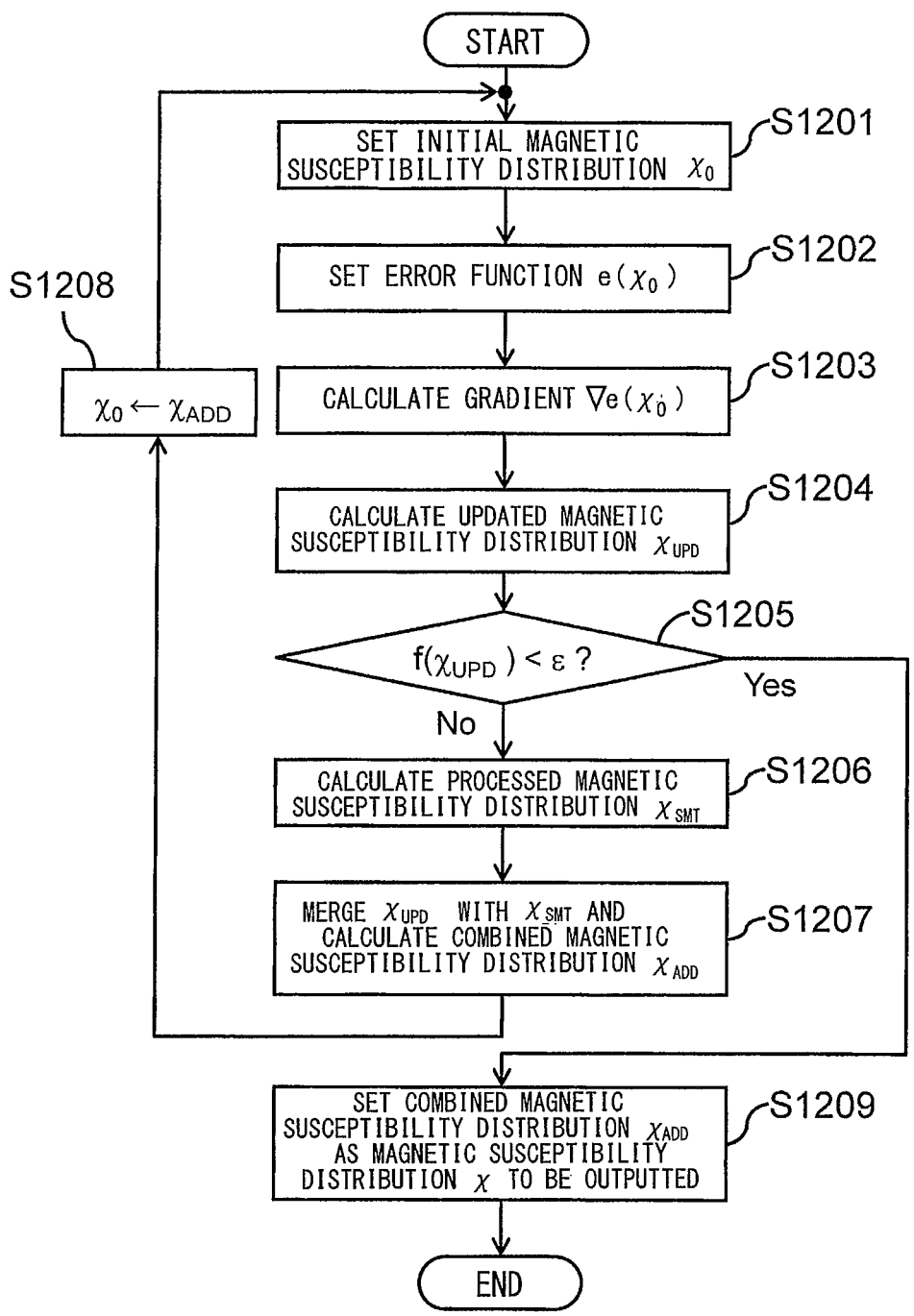
FIG. 7 is a flowchart of the process for calculating a magnetic susceptibility distribution according to an embodiment of the present invention.
Figure 8:
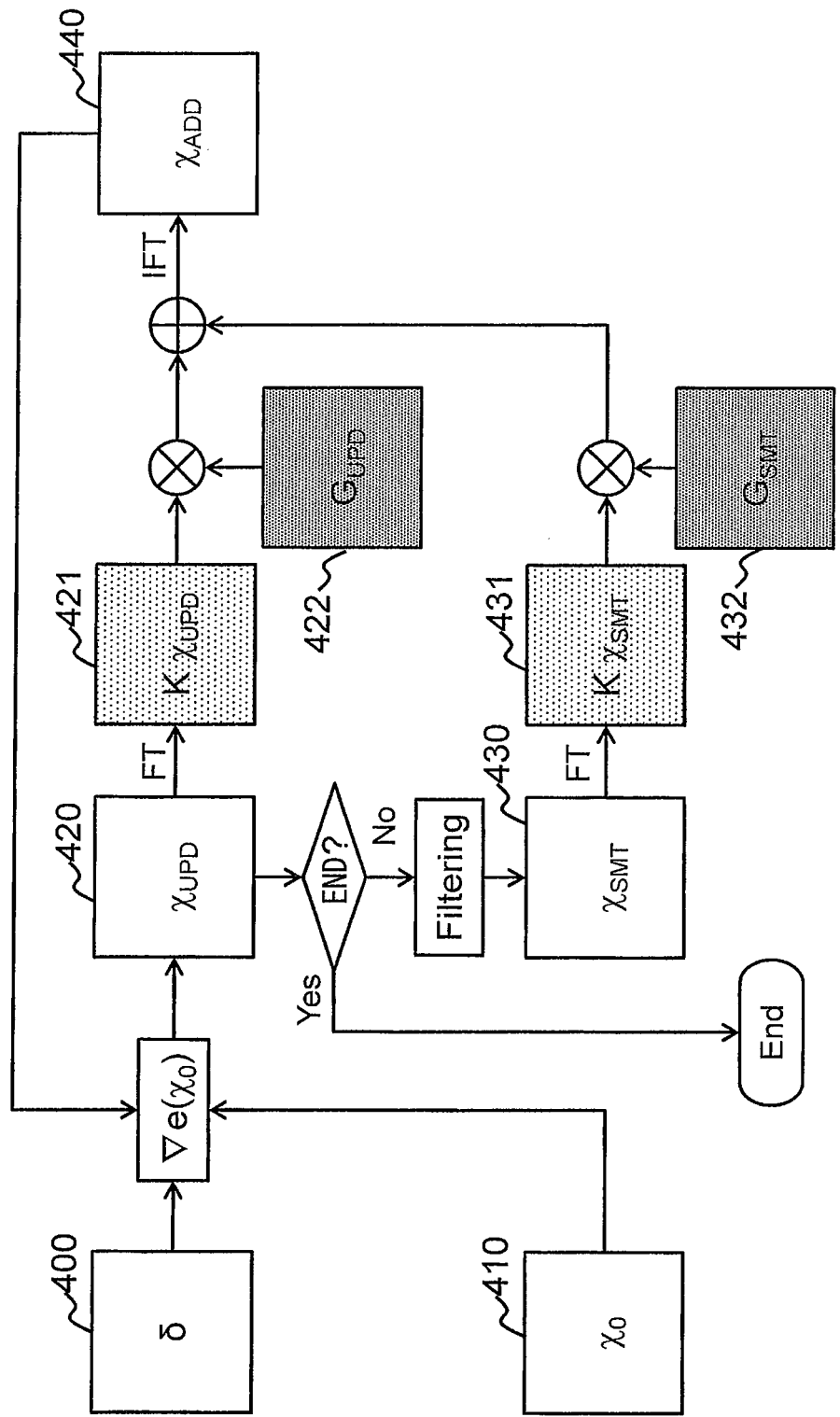
FIG. 8 illustrates a flow of the process for calculating the magnetic susceptibility distribution according to an embodiment of the present invention.

Next, a flow of the magnetic susceptibility distribution calculating process according to the magnetic susceptibility distribution calculator 340 of the present embodiment will be described. FIG. 7 is a flowchart of the magnetic susceptibility distribution calculating process according to the present embodiment. FIG. 8 illustrates the magnetic susceptibility distribution calculating process.

In the present embodiment, the minimization process for minimizing the error function defined by the predetermined initial magnetic susceptibility distribution $\chi_0$ and the magnetic field distribution $\delta$, is performed through the iterative operation, thereby calculating the magnetic susceptibility distribution $\chi$. At this time, during the minimization process, the smoothing process is performed on the updated magnetic susceptibility distribution calculated from the error function, whereby the combined magnetic susceptibility distribution is obtained, updating the initial magnetic susceptibility distribution with the combined magnetic susceptibility distribution, and then the process is repeated. Specifically, the following process is performed.

The magnetic susceptibility distribution calculator 340 provides the initial magnetic susceptibility distribution $\chi_0$ 410 (step S1201). Then, the error function setter 341 utilizes the initial magnetic susceptibility distribution $\chi_0$ 410 and the magnetic field distribution $\delta$ 400, so as to provide the error function $e(\chi_0)$ (step S1202).

Then, the updated magnetic susceptibility distribution calculator 342 calculates the gradient $\nabla e(\chi_0)$ of the error function (step S1203) and according to the aforementioned formula 8, the initial magnetic susceptibility distribution $\chi_0$ is updated, whereby the updated magnetic susceptibility distribution $\chi_{UPD}$ 420 is calculated (step S1204).

The determiner 346 utilizes the evaluation function $f(\chi_{UPD})$ according to the aforementioned formula 11, and determines if the operation ends (step S1205).

When it is determined that the operation continues in step S1205, the filter processor 344 applies the predetermined smoothing filter to the updated magnetic susceptibility distribution $\chi_{UPD}$ 420 (Filtering), thereby calculating the processed magnetic susceptibility distribution $\chi_{SMT}$ 430 (step S1206).

The combiner 345 merges the updated magnetic susceptibility distribution $\chi_{UPD}$ 420 with the processed magnetic susceptibility distribution $\chi_{SMT}$ 430, and the combined magnetic susceptibility distribution $\chi_{ADD}$ 440 is obtained (step S1207). Merging is performed by multiplying k-space data items 421 and 431, obtained through Fourier transform of the updated magnetic susceptibility distribution $\chi_{UPD}$ 420 and the processed magnetic susceptibility distribution $\chi_{SMT}$ 430, respectively, by the weighted images 422 and 432 according to the aforementioned formula 10, adding the products together, followed by inverse Fourier transform (IFT) on the result of the weighted addition.

The determiner 346 sets the combined magnetic susceptibility distribution $\chi_{ADD}$ 440 as the initial magnetic susceptibility distribution $\chi_0$ 410 (step S1208), returning to step S1202, and the process is repeated.

When the end of the operation is determined in step S1205, the determiner 346 assumes the latest combined magnetic susceptibility distribution $\chi_{ADD}$ obtained at that point of time, as the magnetic susceptibility distribution $\chi$ outputted by the magnetic susceptibility distribution calculator 340 (step S1209), and finishes the process.

If the combined magnetic susceptibility distribution $\chi_{ADD}$ is not obtained in step S1205, i.e., when the end of the operation is determined in the first operation, the combined magnetic susceptibility distribution $\chi_{ADD}$ is calculated from the updated magnetic susceptibility distribution $\chi_{UPD}$ at that point of time according to the aforementioned method, and this calculated combined magnetic susceptibility distribution $\chi_{ADD}$ is assumed as the magnetic susceptibility distribution $\chi$ to be outputted.

<Modification Example of Magnetic Susceptibility Distribution Calculating Process Flow>

The determiner 346 may utilize the combined magnetic susceptibility distribution $\chi_{ADD}$ to determine if it is the end of the operation. In other words, it is also possible that when the combined magnetic susceptibility distribution $\chi_{ADD}$ is calculated, the combined magnetic susceptibility distribution $\chi_{ADD}$ and the initial magnetic susceptibility distribution $\chi_0$ at this point of time are used to determine the end of the operation.

In this case, as the evaluation function for determining the end of the operation, $f(\chi_{ADD})$ as the following is employed.

[Formula 12]

$$f(\chi_{ADD}) = \frac{\|\chi_{ADD} - \chi_0\|_2}{\|\chi_0\|_2} < \varepsilon \qquad (12)$$

Figure 9:
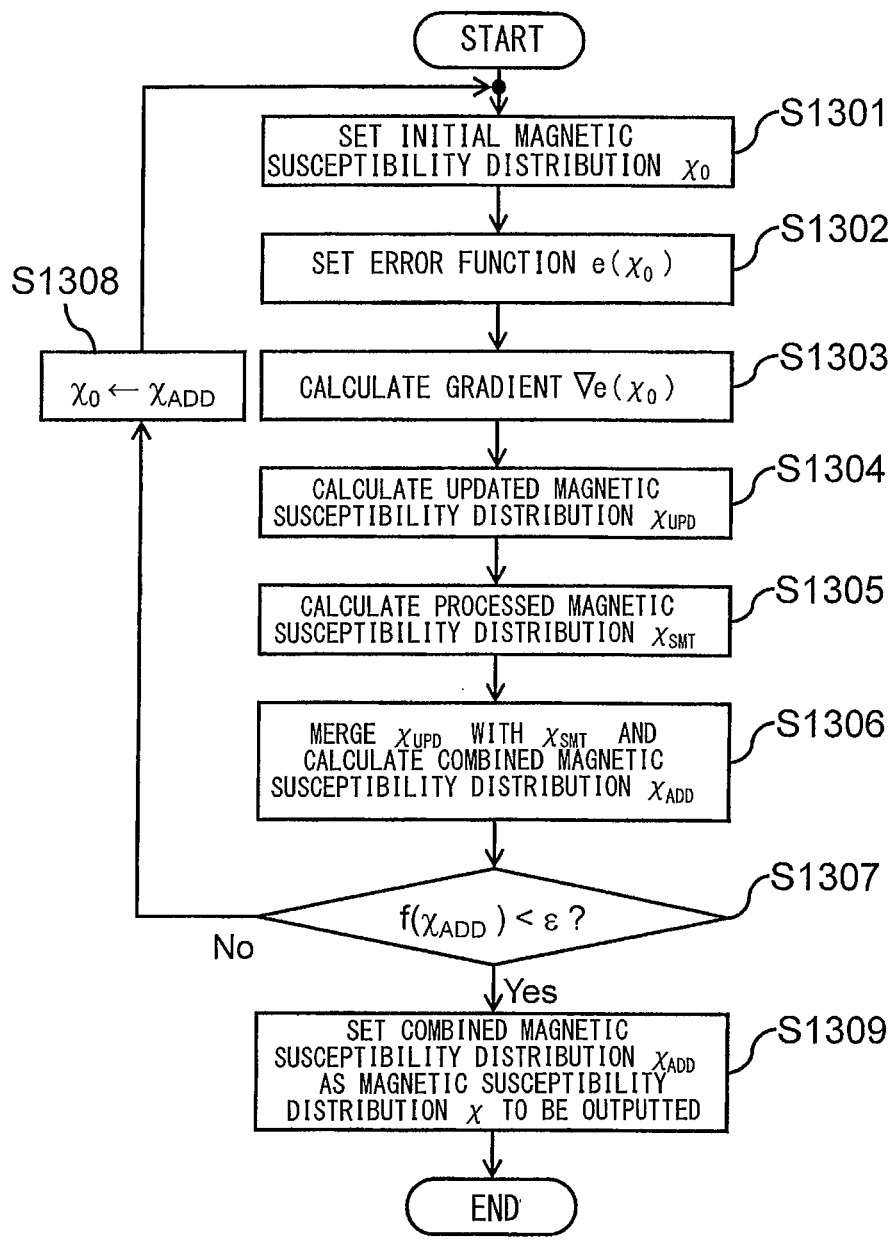
FIG. 9 is a flowchart of the process for calculating the magnetic susceptibility distribution according to a modification of an embodiment of the present invention.
Figure 10:
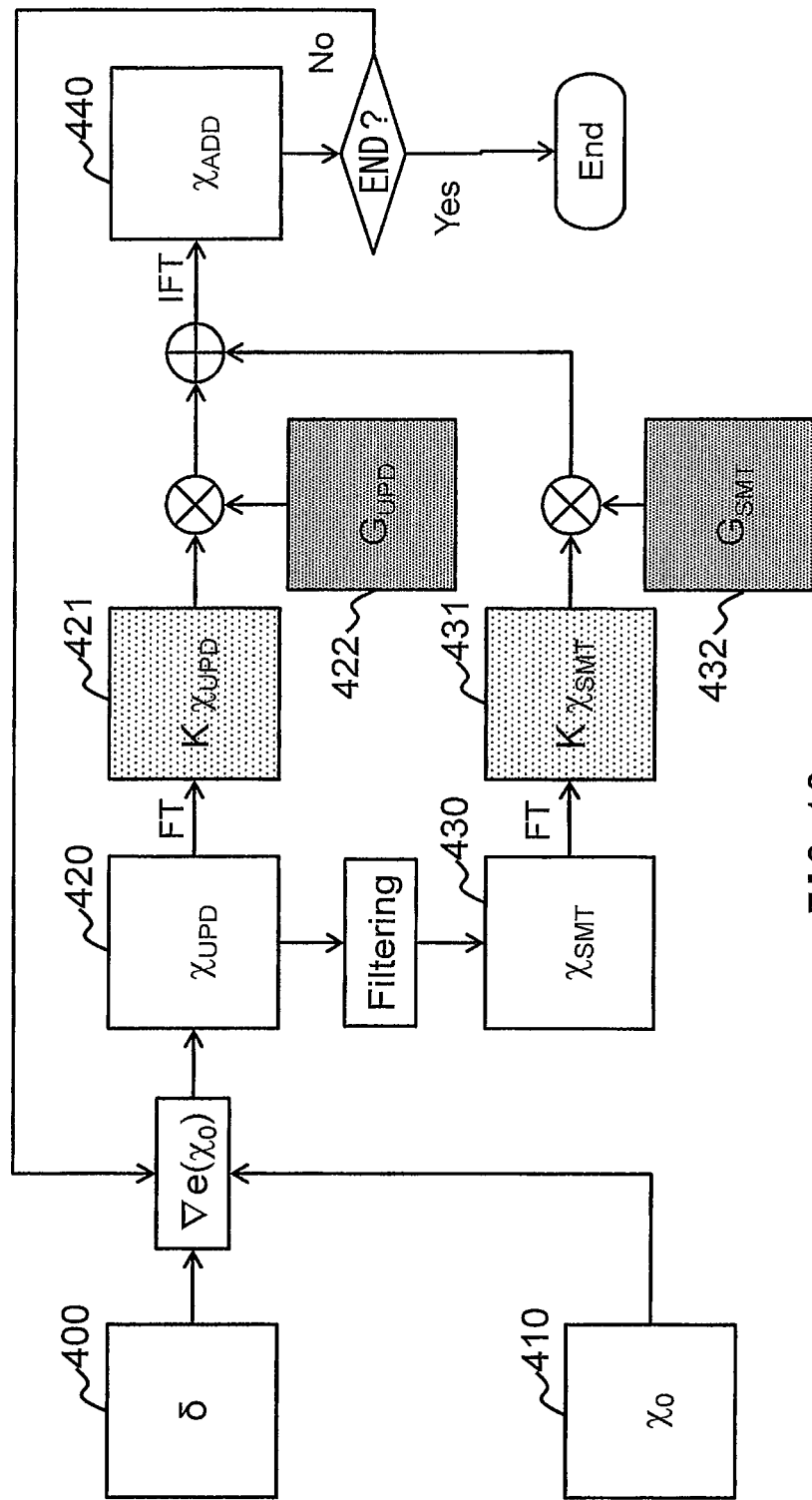
FIG. 10 illustrates a flow of the process for calculating the magnetic susceptibility distribution according to the modification of the embodiment of the present invention.

FIG. 9 is a flowchart of the magnetic susceptibility distribution calculating process according to each unit of the magnetic susceptibility distribution calculator 340. FIG. 10 is an illustration showing this process.

The magnetic susceptibility distribution calculator 340 provides the initial magnetic susceptibility distribution $\chi_0$ 410 (step S1301). Then, the error function setter 341 utilizes the initial magnetic susceptibility distribution $\chi_0$ 410 and the magnetic field distribution $\delta$ 400, so as to provide the error function $e(\chi_0)$ (step S1302).

Next, the updated magnetic susceptibility distribution calculator 342 calculates the gradient $\nabla e(\chi_0)$ of the error function (step S1303), and calculates the updated magnetic susceptibility distribution $\chi_{UPD}$ 420 according to the formula 8 (step S1304).

The filter processor 344 applies the predetermined smoothing filter to the updated magnetic susceptibility distribution $\chi_{UPD}$ 420 (Filtering), thereby calculating the processed magnetic susceptibility distribution $\chi_{SMT}$ 430 (step S1305).

The combiner 345 merges the updated magnetic susceptibility distribution $\chi_{UPD}$ 420 with the processed magnetic susceptibility distribution $\chi_{SMT}$ 430, whereby the combined magnetic susceptibility distribution $\chi_{ADD}$ 440 is obtained (step S1306). Merging is performed by multiplying the k-space data items 421 and 431, obtained through Fourier transform of the updated magnetic susceptibility distribution $\chi_{UPD}$ 420 and the processed magnetic susceptibility distribution $\chi_{SMT}$ 430, respectively, by the weighted images 422 and 432 according to the aforementioned formula 10, adding the products together, followed by inverse Fourier transform (IFT) on the result of the weighted addition.

Next, the determiner 346 utilizes the evaluation function $f(\chi_{ADD})$ of the formula 12, so as to determine the end of the operation (step S1307).

When it is determined the operation continues in step S1307, the magnetic susceptibility distribution calculator 340 sets the combined magnetic susceptibility distribution $\chi_{ADD}$ 440 as the initial magnetic susceptibility distribution $\chi_0$ 410 (step S1308), returning to step S1302, and the process is repeated.

When the end of the operation is determined in step S1307, the latest combined magnetic susceptibility distribution $\chi_{ADD}$ obtained at that point of time is assumed as the magnetic susceptibility distribution $\chi$ outputted by the magnetic susceptibility distribution calculator 340 (step S1309), and the process is finished.

If the determination is made according to the combined magnetic susceptibility distribution $\chi_{ADD}$, it is possible to obtain an image with a large effect of the filtering process, relative to the case where the determination is made according to the updated magnetic susceptibility distribution $\chi_{UPD}$. On the other hand, if the determination is made according to the updated magnetic susceptibility distribution $\chi_{UPD}$, it is determined by data closer to an actual magnetic susceptibility distribution, relative to the case where the determination is made by the combined magnetic susceptibility distribution $\chi_{ADD}$, and therefore this allows the determination on the basis of more appropriate scope of data.

As described above, the MRI apparatus of the present embodiment is provided with, the measurement controller 310 configured to measure the complex signals of the nuclear magnetic resonance signals generated from the subject 101, in response to irradiation with RF magnetic field pulses, the image reconstructor 320 configured to reconstruct from the complex signals, the complex image I including the pixel value which is a complex number, the magnetic field distribution calculator 330 configured to generate the phase image P from the complex image I and to calculate the magnetic field distribution δ from the phase image P, and the magnetic susceptibility distribution calculator 340 configured to calculate the magnetic susceptibility distribution $\chi$ from the magnetic field distribution δ, wherein, the magnetic susceptibility distribution calculator 340 performs the minimization process for minimizing through the iterative operation, the error function $e(\chi_0)$ defined by the predetermined initial magnetic susceptibility distribution $\chi_0$ and the magnetic field distribution δ, thereby calculating the magnetic susceptibility distribution $\chi$, and performs smoothing on the updated magnetic susceptibility distribution $\chi_{UPD}$ that is calculated based on the error function $e(\chi_0)$ during the minimization process, every time the updated magnetic susceptibility distribution $\chi_{UPD}$ is calculated.

The magnetic susceptibility distribution calculator 340 is provided with the updated magnetic susceptibility distribution calculator 342 configured to use the error function $e(\chi_0)$ so as to calculate the updated magnetic susceptibility distribution $\chi_{UPD}$ from the initial magnetic susceptibility distribution $\chi_0$, the smoothing processor 343 configured to smooth the updated magnetic susceptibility distribution $\chi_{UPD}$, so as to generate the combined magnetic susceptibility distribution $\chi_{ADD}$, and the determiner 346 configured to determine the end of the iterative operation, and to set the combined magnetic susceptibility distribution $\chi_{ADD}$ as the initial magnetic susceptibility distribution $\chi_0$. The smoothing processor 343 is provided with the filter processor 344 configured to apply the predetermined smoothing filter to the updated magnetic susceptibility distribution $\chi_{UPD}$, so as to obtain the processed magnetic susceptibility distribution $\chi_{SMT}$, and the combiner 345 configured to merge the updated magnetic susceptibility distribution $\chi_{UPD}$ with the processed magnetic susceptibility distribution $\chi_{SMT}$, and to generate the combined magnetic susceptibility distribution $\chi_{ADD}$. The determiner 346 may set the combined magnetic susceptibility distribution $\chi_{ADD}$ as the magnetic susceptibility distribution $\chi$, which is obtained when the end of the operation is determined.

The error function $e(\chi_0)$ is set by assigning the weight W to the function defined by the magnetic field distribution δ and the result of the convolution operation performed on the initial magnetic susceptibility distribution $\chi_0$. The weight W may be calculated based on the phase image P obtained from the complex image I.

As thus described, in the present embodiment, the iterative operation of the smoothing process under the constraint of the relational expression between the magnetic field and the magnetic susceptibility, enables calculation of the highly precise magnetic susceptibility distribution.

In other words, in the present embodiment, the updated magnetic susceptibility distribution $\chi_{UPD}$ is smoothed, which is obtained in the course of the minimization process for minimizing the error function, and this process is repeated. In the smoothing, the processed magnetic susceptibility distribution $\chi_{SMT}$ smoothed by the smoothing filter and the updated magnetic susceptibility distribution $\chi_{UPD}$ calculated by using the gradient of the error function, are weighted in k-space and merged together, so that noise is reduced and the fine structure is maintained.

As described above, in the present embodiment, data of noise part is averaged by filtering according to the smoothing filter, allowing the noise in the calculated magnetic susceptibility distribution $\chi$ to be reduced. Further, according to the merging process, the fine structure can be maintained in the magnetic susceptibility distribution $\chi$.

Unlike the conventional methods, a regularization term is not used in the present embodiment, and thus it is possible to obtain the magnetic susceptibility distribution $\chi$ where noise is reduced along with maintaining the fine structure, through the simple process. In other words, according to the present embodiment, enormous calculations for setting adequate regularization parameters are not required.

According to the present embodiment, values in the vicinity of the magic angle region are not truncated in solving the ill-conditioned problem. Therefore, artifacts caused by this truncation may be reduced, thereby enhancing accuracy of thus calculated magnetic susceptibility distribution.

It should be further noted that the processed magnetic susceptibility distribution $\chi_{SMT}$ used for reducing noise and maintaining the fine structure in the updated magnetic susceptibility distribution $\chi_{UPD}$, and the combined magnetic susceptibility distribution $\chi_{ADD}$ for updating the initial magnetic susceptibility distribution $\chi_0$ in the iterative operation, are both calculated from the updated magnetic susceptibility distribution $\chi_{UPD}$. In other words, these are data items that depend on phase information.

In the present embodiment, such data depending on the phase information is used to update the magnetic susceptibility distribution calculated through the iterative operation of the minimization process, and thus this yields an advantage that inconsistencies may be reduced between the measured phase information and the magnetic susceptibility distribution being calculated.

According to the present embodiment, the weight W in the error function is calculated from the phase image. The phase image is higher in precision in reflecting the phase fluctuation, relative to an absolute value image, and thus, it is possible to obtain the weight W on which this phase fluctuation is reflected precisely. Since the magnetic susceptibility distribution $\chi$ is calculated according to the error function using this weight, the magnetic susceptibility distribution can be calculated with a higher degree of precision.

As described above, according to the present embodiment, smoothing process is repeated through the simple process, preserving edge information such as the fine structure along with maintaining the relationship between the magnetic field and the magnetic susceptibility, thereby reducing artifacts and noise, and enhancing accuracy and precision of the magnetic susceptibility distribution being calculated.

<Modification Example of Weighted Image in Merging>

The weighted image G which is used when the combiner 345 merges the updated magnetic susceptibility distribution $\chi_{UPD}$ with the processed magnetic susceptibility distribution $\chi_{SMT}$, is not limited to the weighted images as described above. By way of example, $G_{UPD}(k)$ and $G_{SMT}(k)$ may be constant values, respectively. That is, the entire data within each k-space may be weighted homogeneously.

Assignment of the unique weight may allow easy control of SNR (signal-to-noise) of the image that is ultimately obtained.

<Modification Example of Weight in the Error Function>

In the aforementioned embodiment, the weight W in the error function $e(\chi_0)$ that is provided by the error function setter 341 is calculated from the phase value component of the complex image I, but this is not the only example. The weight W may be calculated from an absolute value component of the complex image I. Calculation from the absolute value component may allow the weight to be obtained through an easy and simple process.

DESCRIPTION OF SYMBOLS

100: MRI apparatus, 101: test subject, 102: static magnetic field coil, 103: gradient magnetic field coil, 104: shim coil, 105: transmitter coil, 106: receiver coil, 107: transmitter, 108: receiver, 109: computer, 110: display, 111: external storage device, 112: gradient magnetic field power supply, 113: shim power supply, 114: sequence controller, 115: input device, 120: MRI apparatus, 130: MRI apparatus, 310: measurement controller, 320: image reconstructor, 330: magnetic field distribution calculator, 331: phase image calculator, 332: phase unwrapping processor, 333: global phase change eliminator, 334: magnetic field distribution converter, 340: magnetic susceptibility distribution calculator, 341: the error function setter, 342: updated magnetic susceptibility distribution calculator, 343: smoothing processor, 344: filter processor, 345: combiner, 346: determiner, 400: magnetic field distribution, 410: initial magnetic susceptibility distribution, 420: updated magnetic susceptibility distribution, 421: k-space data of updated magnetic susceptibility distribution, 422: weighted image by which updated magnetic susceptibility distribution is multiplied, 430: processed magnetic susceptibility distribution, 431: k-space data of processed magnetic susceptibility distribution, 432: weighted image by which processed magnetic susceptibility distribution is multiplied, 440: combined magnetic susceptibility distribution, 501: slice gradient magnetic field pulse, 502: RF pulse, 503: slice encoding gradient magnetic field pulse, 504: phase encoding gradient magnetic field pulse, 505: readout gradient magnetic field pulse, 506: readout gradient magnetic field pulse, 507: echo, 508: slice encoding gradient magnetic field pulse, 509: phase encoding gradient magnetic field pulse, 510: RSSG sequence

What is claimed is:

1. A magnetic resonance imaging apparatus comprising,
a measurement controller configured to measure complex signals of nuclear magnetic resonance signals generated from a subject in response to irradiation of RF magnetic field pulses,
an image reconstructor configured to reconstruct a complex image where a pixel value is a complex value, from the complex signals measured by the measurement controller,
a magnetic field distribution calculator configured to generate a phase image from the complex image, and to calculate a magnetic field distribution from the phase image, and
a magnetic susceptibility distribution calculator configured to calculate a magnetic susceptibility distribution from the magnetic field distribution,
wherein the magnetic susceptibility distribution calculator performs a minimization process for minimizing through an iterative operation, an error function defined by a predetermined initial magnetic susceptibility distribution and the magnetic field distribution, thereby calculating the magnetic susceptibility distribution, and performs smoothing on an updated magnetic susceptibility distribution that is calculated based on the error function during the minimization process, every time the updated magnetic susceptibility distribution is calculated;
wherein the magnetic susceptibility distribution calculator comprises
an updated magnetic susceptibility distribution calculator configured to use the error function so as to calculate the updated magnetic susceptibility distribution from the initial magnetic susceptibility distribution,
a smoothing processor configured to smooth the updated magnetic susceptibility distribution, so as to generate a combined magnetic susceptibility distribution, and
a determiner configured to determine an end of the iterative operation, and to set the combined magnetic susceptibility distribution as the initial magnetic susceptibility distribution; and wherein the determiner sets the combined magnetic susceptibility distribution obtained when the end of the operation is reached, as the magnetic susceptibility distribution.

2. The magnetic resonance imaging apparatus according to claim 1, wherein,
the smoothing processor comprises,
a filter processor configured to apply a predetermined smoothing filter to the updated magnetic susceptibility distribution, so as to obtain a processed magnetic susceptibility distribution, and
a combiner configured to merge the updated magnetic susceptibility distribution with the processed magnetic susceptibility distribution, and to generate the combined magnetic susceptibility distribution.

3. The magnetic resonance imaging apparatus according to claim 1, wherein,
the error function is provided by assigning a weight to a function defined by the magnetic field distribution and a result of a convolution operation that is performed on the initial magnetic susceptibility distribution, and
the weight is calculated on the basis of the phase image obtained from the complex image.

4. The magnetic resonance imaging apparatus according to claim 1, wherein,
the magnetic susceptibility distribution calculator calculates a gradient of the error function, and calculates the updated magnetic susceptibility distribution by using the gradient thus obtained.

5. The magnetic resonance imaging apparatus according to claim 2, wherein,
the combiner converts the updated magnetic susceptibility distribution and the processed magnetic susceptibility distribution, respectively, into k-space data, and the k-space data of the updated magnetic susceptibility distribution and the k-space data of the processed magnetic susceptibility distribution after the conversion are weighted and added together, thereby generating the combined magnetic susceptibility distribution.

6. The magnetic resonance imaging apparatus according to claim 5, wherein,
in the k-space data of the updated magnetic susceptibility distribution, the weight assigned to the data in the vicinity of a magic angle region is set smaller than the weight assigned to another region, and
in the k-space data of the processed magnetic susceptibility distribution, the weight assigned to the data in the vicinity of the magic angle region is set larger than the weight assigned to the data in another region.

7. The magnetic resonance imaging apparatus according to claim 5, wherein,
the weight is assigned to entire data homogeneously in each of the k-space data.

8. The magnetic resonance imaging apparatus according to claim 1, wherein,
the smoothing filter is an edge preserving smoothing filter.

9. The magnetic resonance imaging apparatus according to claim 1, wherein,
every value in the initial magnetic susceptibility distribution is zero.

10. The magnetic resonance imaging apparatus according to claim 1, wherein,
when the updated magnetic susceptibility distribution is calculated, the determiner uses the updated magnetic susceptibility distribution and the initial magnetic susceptibility distribution, so as to determine the end of the operation.

11. The magnetic resonance imaging apparatus according to claim 1, wherein,
when the combined magnetic susceptibility distribution is calculated, the determiner uses the combined magnetic susceptibility distribution and the initial magnetic susceptibility distribution, so as to determine the end of the operation.

12. A quantitative magnetic susceptibility mapping method comprising,
collecting nuclear magnetic resonance signals generated from a subject in response to irradiation of RF magnetic field pulses, so as to obtain a phase image from a magnetic resonance image that is a complex image acquired by reconstructing the signals,
calculating a magnetic field distribution from the phase image, and
performing a minimization process through an iterative operation, for minimizing an error function defined by a predetermined initial magnetic susceptibility distribution and the magnetic field distribution, so as to obtain a magnetic susceptibility distribution, and
during the minimization process,
smoothing an updated magnetic susceptibility distribution obtained by updating the initial magnetic susceptibility distribution, calculated from the error function, and obtaining a combined magnetic susceptibility distribution,
wherein the updated magnetic susceptibility distribution is calculated from the initial magnetic susceptibility distribution using the error function,
wherein the updated magnetic susceptibility distribution is smoothed so as to generate the combined magnetic susceptibility distribution,
determining an end of the iterative operation, and updating the initial magnetic susceptibility distribution to the combined magnetic susceptibility distribution, and
setting the combined magnetic susceptibility distribution obtained when the end of the operation is reached, as the magnetic susceptibility distribution.

13. The quantitative magnetic susceptibility mapping method according to claim 12, wherein,
the error function is provided by assigning a weight to a function defined by the magnetic field distribution and a result of a convolution operation that is performed on the initial magnetic susceptibility distribution, and
the weight is calculated on the basis of the phase image obtained from the complex image.

14. The quantitative magnetic susceptibility mapping method according to claim 12, wherein smoothing the updated magnetic susceptibility distribution comprises:
applying a predetermined smoothing filter to the updated magnetic susceptibility distribution, so as to obtain a processed magnetic susceptibility distribution, and
merging the updated magnetic susceptibility distribution with the processed magnetic susceptibility distribution to generate the combined magnetic susceptibility distribution.

15. The quantitative magnetic susceptibility mapping method according to claim 14, wherein the merging comprises:
converting the updated magnetic susceptibility distribution and the processed magnetic susceptibility distribution, respectively, into k-space data, and the k-space data of the updated magnetic susceptibility distribution and the k-space data of the processed magnetic susceptibility distribution after the conversion are weighted and added together, thereby generating the combined magnetic susceptibility distribution.

16. A calculator which calculates magnetic susceptibility distribution using magnetic resonance signals collected by a magnetic resonance imaging apparatus or using a magnetic resonance image that is a complex image acquired by reconstructing the nuclear magnetic resonance signals, the calculator having a processor programmed to:

generate a phase image from the complex image, and calculate a magnetic field distribution from the phase image, and calculate the magnetic susceptibility distribution by performing a minimization process through an iterative operation, for minimizing an error function defined by a predetermined initial magnetic susceptibility distribution and the magnetic field distribution, smooth an updated magnetic susceptibility distribution that is calculated based on the error function during the minimization process, every time the updated magnetic susceptibility distribution is calculated, wherein the updated magnetic susceptibility distribution is calculated from the initial magnetic susceptibility distribution is smoothed so as to generate the combined magnetic susceptibility distribution, determine an end of the iterative operation, and update the initial magnetic susceptibility distribution to the combined magnetic susceptibility distribution, and set the combined magnetic susceptibility distribution obtained when the end of the operation is reached, as the magnetic susceptibility distribution.

17. The calculator according to claim 16, wherein,
the error function is provided by assigning a weight to a function defined by the magnetic field distribution and a result of a convolution operation that is performed on the initial magnetic susceptibility distribution, and
the weight is calculated on the basis of the phase image obtained from the complex image.

18. The calculator according to claim 16, wherein the processor is programmed to:
apply a predetermined smoothing filter to the updated magnetic susceptibility distribution, so as to obtain a processed magnetic susceptibility distribution, and
merge the updated magnetic susceptibility distribution with the processed magnetic susceptibility distribution, and generate the combined magnetic susceptibility distribution.

19. The calculator according to claim 18, wherein the processor is programmed to:
convert the updated magnetic susceptibility distribution and the processed magnetic susceptibility distribution, respectively, into k-space data, and the k-space data of the updated magnetic susceptibility distribution and the k-space data of the processed magnetic susceptibility distribution after the conversion are weighted and added together, thereby generating the combined magnetic susceptibility distribution.

20. A magnetic resonance imaging apparatus comprising a computer programmed to:
measure complex signals of nuclear magnetic resonance signals generated from a subject in response to irradiation of RF magnetic field pulses,
reconstruct a complex image where a pixel value is a complex value, from the complex signals measured by the measurement controller,
generate a phase image from the complex image, and calculate a magnetic field distribution from the phase image, and
calculate a magnetic susceptibility distribution from the magnetic field distribution,
wherein calculating the magnetic susceptibility distribution includes performing a minimization process for minimizing through an iterative operation, an error function defined by a predetermined initial magnetic susceptibility distribution and the magnetic field distribution, thereby calculating the magnetic susceptibility distribution, calculating a gradient of the error function, calculating an updated magnetic susceptibility distribution by using the gradient thus obtained, and performing smoothing on the updated magnetic susceptibility distribution during the minimization process, every time the updated magnetic susceptibility distribution is calculated.

* * * * *